United States Patent
Pastore et al.

(10) Patent No.: US 7,113,825 B2
(45) Date of Patent: Sep. 26, 2006

(54) METHOD AND APPARATUS FOR DETECTING ACOUSTIC OSCILLATIONS IN CARDIAC RHYTHM

(75) Inventors: Joseph M. Pastore, Minneapolis, MN (US); William C. Lincoln, Coon Rapids, MN (US); Gerrard M. Carlson, Champlin, MN (US); Qingsheng Zhu, Little Canada, MN (US); Jiang Ding, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 674 days.

(21) Appl. No.: 10/138,046

(22) Filed: May 3, 2002

(65) Prior Publication Data

US 2003/0208240 A1    Nov. 6, 2003

(51) Int. Cl.
*A61N 1/39* (2006.01)
*A61B 5/02* (2006.01)

(52) U.S. Cl. ............... 607/14; 607/17; 600/528
(58) Field of Classification Search ........... 600/514, 600/528, 586, 515; 607/14, 17
See application file for complete search history.

(56) References Cited

U.S. PATENT DOCUMENTS

| | | | |
|---|---|---|---|
| 4,291,699 A | 9/1981 | Geddes et al. | |
| 4,674,518 A | 6/1987 | Salo | 128/695 |
| 4,686,987 A | 8/1987 | Salo et al. | 128/419 PG |
| 4,712,179 A | 12/1987 | Heimer | |
| 4,777,960 A | 10/1988 | Berger et al. | |
| 4,802,491 A | 2/1989 | Cohen et al. | |
| 4,809,697 A | 3/1989 | Causey, III et al. | |
| 4,825,869 A | 5/1989 | Sasmor et al. | |
| 4,928,688 A | 5/1990 | Mower | |
| 4,981,139 A | 1/1991 | Pfohl | |
| 5,010,889 A | 4/1991 | Bredesen et al. | |
| 5,012,815 A | 5/1991 | Bennett, Jr. et al. | |
| 5,097,831 A | 3/1992 | Lekholm | |
| 5,113,869 A | 5/1992 | Nappholz et al. | |
| 5,137,019 A | 8/1992 | Pederson et al. | 128/419 |
| 5,174,289 A | 12/1992 | Cohen | |
| 5,179,947 A | 1/1993 | Meyerson et al. | |
| 5,190,035 A | 3/1993 | Salo et al. | 128/419 |
| 5,226,413 A | 7/1993 | Bennett et al. | |
| 5,251,626 A | 10/1993 | Nickolls et al. | |
| 5,265,617 A | 11/1993 | Verrier et al. | |
| 5,282,838 A | 2/1994 | Hauser et al. | |
| 5,284,136 A | 2/1994 | Hauck et al. | 607/24 |
| 5,292,341 A | 3/1994 | Snell | |
| 5,321,618 A | 6/1994 | Gessman | |

(Continued)

FOREIGN PATENT DOCUMENTS

EP    297675 A1    1/1989

(Continued)

OTHER PUBLICATIONS

Arnaud, Claire, et al., "iNOS is a mediator of the heat stress-induced preconditioning against myocardial infarction in vivo in the rat", *Cardiovascular Research*, 58, (2003), 118-125.

(Continued)

*Primary Examiner*—Mark Bockelman
(74) *Attorney, Agent, or Firm*—Schwegman, Lundberg, Woessner & Kluth, P.A.

(57) ABSTRACT

A cardiac rhythm management device is configured to detect oscillations in cardiac rhythm by measuring the amplitudes of heart sounds during successive heart beats. Upon detection of acoustic alternans, the device may adjust its operating behavior to compensate for the deleterious effects of the condition.

24 Claims, 3 Drawing Sheets

U.S. PATENT DOCUMENTS

| | | | |
|---|---|---|---|
| 5,334,222 A | 8/1994 | Salo et al. .................... 607/17 |
| 5,368,040 A | 11/1994 | Carney et al. |
| 5,372,607 A | 12/1994 | Stone et al. |
| 5,391,190 A | 2/1995 | Pederson et al. ............. 607/23 |
| 5,417,717 A | 5/1995 | Salo et al. .................... 607/18 |
| 5,421,830 A | 6/1995 | Epstein et al. |
| 5,487,752 A | 1/1996 | Salo et al. .................... 607/17 |
| 5,540,727 A | 7/1996 | Tockman et al. |
| 5,549,654 A | 8/1996 | Powell |
| 5,554,177 A | 9/1996 | Kieval et al. |
| 5,564,434 A | 10/1996 | Halperin et al. |
| 5,584,868 A | 12/1996 | Salo et al. .................... 607/17 |
| 5,594,638 A | 1/1997 | Iliff |
| 5,607,460 A | 3/1997 | Kroll et al. |
| 5,630,835 A | 5/1997 | Brownlee |
| 5,674,256 A | 10/1997 | Carlson |
| 5,690,690 A | 11/1997 | Nappholz et al. |
| 5,700,283 A | 12/1997 | Salo |
| 5,713,367 A | 2/1998 | Arnold et al. |
| 5,716,382 A | 2/1998 | Snell |
| 5,720,771 A | 2/1998 | Snell |
| 5,722,999 A | 3/1998 | Snell |
| 5,724,985 A | 3/1998 | Snell et al. |
| 5,749,900 A | 5/1998 | Schroeppel et al. |
| 5,759,199 A | 6/1998 | Snell et al. |
| 5,792,195 A | 8/1998 | Carlson et al. |
| 5,800,473 A | 9/1998 | Faisandier |
| 5,824,029 A | 10/1998 | Weijand et al. |
| 5,833,623 A | 11/1998 | Mann et al. |
| 5,836,974 A | 11/1998 | Christini et al. |
| 5,836,987 A | 11/1998 | Baumann et al. |
| 5,860,918 A | 1/1999 | Schradi et al. |
| 5,882,312 A | 3/1999 | Gopakumaran et al. |
| 5,891,178 A | 4/1999 | Mann et al. |
| 5,904,708 A | 5/1999 | Goedeke |
| 5,919,210 A | 7/1999 | Lurie et al. |
| 5,921,940 A | 7/1999 | Verrier et al. |
| 5,935,081 A | 8/1999 | Kadhiresan |
| 6,015,388 A | 1/2000 | Sackner et al. |
| 6,016,442 A | 1/2000 | Hsu et al. |
| 6,022,322 A | 2/2000 | Prutchi ....................... 600/506 |
| 6,026,324 A | 2/2000 | Carlson |
| 6,035,233 A | 3/2000 | Schroeppel et al. |
| 6,044,298 A | 3/2000 | Salo et al. |
| 6,044,299 A | 3/2000 | Nilsson |
| 6,058,328 A | 5/2000 | Levine et al. |
| 6,058,329 A | 5/2000 | Salo et al. |
| 6,070,101 A | 5/2000 | Struble et al. |
| 6,091,990 A | 7/2000 | Hsu et al. |
| 6,144,880 A | 11/2000 | Ding et al. |
| 6,161,042 A | 12/2000 | Hartley et al. ................ 607/20 |
| 6,168,563 B1 | 1/2001 | Brown |
| 6,190,324 B1 | 2/2001 | Kieval et al. |
| 6,193,668 B1 | 2/2001 | Chassaing et al. |
| 6,224,553 B1 | 5/2001 | Nevo |
| 6,240,317 B1 | 5/2001 | Villaseca et al. |
| 6,253,107 B1 | 6/2001 | Albrecht et al. |
| 6,272,377 B1 | 8/2001 | Sweeney et al. |
| 6,275,727 B1 | 8/2001 | Hopper et al. |
| 6,278,894 B1 | 8/2001 | Salo et al. .................. 600/547 |
| 6,280,409 B1 | 8/2001 | Stone et al. |
| 6,285,898 B1 | 9/2001 | Ben-Haim |
| 6,292,694 B1 | 9/2001 | Schloss et al. |
| 6,304,773 B1 | 10/2001 | Taylor et al. |
| 6,336,903 B1 | 1/2002 | Bardy |
| 6,351,673 B1 | 2/2002 | Ding et al. |
| 6,351,675 B1 | 2/2002 | Tholen et al. |
| 6,360,127 B1 | 3/2002 | Ding et al. |
| 6,361,522 B1 | 3/2002 | Scheiner et al. ............. 604/67 |
| 6,366,811 B1 | 4/2002 | Carlson |
| 6,368,284 B1 | 4/2002 | Bardy |
| 6,370,424 B1 | 4/2002 | Prutchi ....................... 600/547 |
| 6,383,136 B1 | 5/2002 | Jordan |
| 6,398,728 B1 | 6/2002 | Bardy |
| 6,409,675 B1 | 6/2002 | Turcott |
| 6,411,840 B1 | 6/2002 | Bardy |
| 6,411,847 B1 | 6/2002 | Mower |
| 6,438,407 B1 | 8/2002 | Ousdigian et al. |
| 6,438,408 B1 | 8/2002 | Mulligan et al. |
| 6,440,066 B1 | 8/2002 | Bardy |
| 6,442,433 B1 | 8/2002 | Linberg |
| 6,453,191 B1 | 9/2002 | Krishnamachari |
| 6,454,707 B1 | 9/2002 | Casscells, III et al. |
| 6,477,406 B1 | 11/2002 | Turcott |
| 6,478,746 B1 | 11/2002 | Chassaing et al. |
| 6,480,733 B1 | 11/2002 | Turcott |
| 6,491,639 B1 | 12/2002 | Turcott |
| 6,520,924 B1 | 2/2003 | Lee |
| 6,527,729 B1 | 3/2003 | Turcott |
| 6,542,775 B1 | 4/2003 | Ding et al. |
| RE38,119 E | 5/2003 | Mower |
| 6,626,842 B1 | 9/2003 | Oka |
| 6,643,548 B1 | 11/2003 | Mai et al. |
| 6,650,940 B1 | 11/2003 | Zhu et al. |
| 6,684,103 B1 | 1/2004 | Ding et al. |
| 6,915,157 B1 | 7/2005 | Bennett et al. |
| 6,957,105 B1 | 10/2005 | Pastore et al. |
| 2001/0007053 A1 | 7/2001 | Bardy |
| 2001/0012955 A1 | 8/2001 | Goedeke et al. |
| 2001/0047125 A1 | 11/2001 | Quy |
| 2002/0016550 A1 | 2/2002 | Sweeney et al. |
| 2002/0019586 A1 | 2/2002 | Teller et al. |
| 2002/0026103 A1 | 2/2002 | Norris et al. |
| 2002/0026223 A1 | 2/2002 | Riff et al. |
| 2002/0123672 A1 | 9/2002 | Christophersom et al. |
| 2002/0151938 A1 | 10/2002 | Corbucci |
| 2003/0023278 A1 | 1/2003 | Pastore et al. |
| 2003/0055461 A1 | 3/2003 | Girouard et al. |
| 2003/0105496 A1 | 6/2003 | Yu et al. |
| 2003/0153952 A1 | 8/2003 | Auricchio et al. |
| 2003/0171791 A1 | 9/2003 | KenKnight et al. |
| 2003/0187482 A1 | 10/2003 | Pastore et al. |
| 2003/0233132 A1 | 12/2003 | Pastore et al. |
| 2004/0054381 A1 | 3/2004 | Pastore et al. |
| 2004/0073093 A1 | 4/2004 | Hatlestad |
| 2004/0093034 A1 | 5/2004 | Girouard et al. |
| 2004/0098057 A1 | 5/2004 | Pastore |
| 2004/0106960 A1 | 6/2004 | Siejko et al. |
| 2004/0106961 A1 | 6/2004 | Siejko et al. |
| 2004/0122484 A1 | 6/2004 | Hatlestad et al. |
| 2004/0127792 A1 | 7/2004 | Siejko et al. |
| 2005/0256542 A1 | 11/2005 | Pastore et al. |
| 2006/0020294 A1 | 1/2006 | Brockway et al. |

FOREIGN PATENT DOCUMENTS

| | | |
|---|---|---|
| EP | 709058 A1 | 5/1996 |
| WO | WO-97/25098 A1 | 7/1997 |
| WO | WO-00/04947 A2 | 2/2000 |
| WO | WO-0041765 A1 | 7/2000 |
| WO | WO-0041766 A1 | 7/2000 |
| WO | WO-01/03575 A1 | 1/2001 |
| WO | WO-01/08748 A1 | 2/2001 |
| WO | WO-01/24876 A1 | 4/2001 |
| WO | WO-01/30436 A2 | 5/2001 |
| WO | WO-0156651 A1 | 8/2001 |
| WO | WO-0167948 A2 | 9/2001 |
| WO | WO-2005122902 A1 | 12/2005 |

OTHER PUBLICATIONS

Barbaro, V., et al., "A portable unit for remote monitoring of pacemaker patients", *Journal of Telemedicine and Telecare*, 3(2), (1997),96-102.

Bourge, Robert, et al., "Noninvasive Rejection Monitoring of Cardiac Transplants Using High Resolution Intramyocardial Electrograms", *PACE*, vol. 221, Part II, (Nov. 1998),2338-2344.

Brockway, Marina, et al., "Method and Apparatus for Monitoring Heart Failure Patients with Cardiopulmonary Comorbidites", U.S. Appl. No. 10/897,856, Filed Jul. 23, 2004, 54 pages.

Brockway, Marina, et al., "Method and Apparatus for Optimization of Cardiac Resynchronization Therapy Using Heart Sounds", U.S. Appl. No. 10/865,498, Filed Jun. 10, 2004, 45 pgs.

Brunner, Friedrich, "Attenuation of myocardial ischemia/reperfusion injury in mice with myocyte-specific overexpression of endothelial nitric oxide synthase", *Cardiovascular Research*, 57, (2003),55-62.

Ferdinandy, Peter, et al., "Nitric oxide, superoxide, and peroxynitrite in myocardial ischaemia-reperfusion injury and preconditioning", *British Journal of Pharmacology*, 138(4), (2003),532-543.

Flögel, Ulrich, "Myoglobin: A scanvenger of bioactive NO", *PNAS*, 98(2), (Jan. 16, 2001),735-740.

Gewaltig, Michael T., "Vasoprotection by nitric oxide: mechanisms and therapeutic potential", *Cardiovascular Research*, 55, (Feb. 14, 2002),250-260.

Hutten, H., et al., "Cardiac pacemaker as bridge to cardiac telemonitoring", *Biomedizinische Technik, 41(6), Institut for Elektro-und Biomedizinische Technik Technische Universitat Graz. English Abstract*, (Jun. 1996), 158-165.

Hutten, H., et al., "Cardiac Telemonitoriing through the Lingkage of Close-up Telemetry and Internet Transmission", *Institute for Electro-and Biomedical Technology, Technical University of Grasz Inffeldgasse, 42 English Abstract*, (1997),67-69.

Ji, J., "An Ultraminiature CMOS Pressure Sensor for a Multiplexed Cardiovascular Catheter", *IEEE Transactions on Electron Devices*, vol. 39, No. 10, (Oct., 1992),pp. 2260-2267.

Kinderman, Michael, et al., "Optimizing the AV Delay in DDD Pacemaker Patients with High Degree AV Block: Mitral Valve Doppler Versus Impedance Cardiography", *PACE*, vol. 20, pp. 2453-2462, (Oct. 1997),2453-2462.

Leonelli, Fabio M., et al., "Systolic and Diastolic Effects of Variable Atroventricular Delay and Patients with Complete Hear Block and Normal Ventricular Function", *Amer. J-Cardiology*, vol. 80, pp. 294-298, (Aug. 1, 1997),294-298.

Li, Qianghong, "Gene Therapy With Inducible Nitric Oxide Synthase Protects Against Myocardial Infarction via a Cyclooxygenase-2-Dependent Mechanism", *Circulation Research*, 92, (2003),741-748.

Maile, Keith R., et al., "A Dual-Use Sensor for Rate Responsive Pacing and Heart Sound Monitoring", U.S. Appl. No. 10/703,175, Filed Nov. 6, 2003, 41 pgs.

Maile, Keith R., et al., "Determining a Patient's Posture from Mechanical Vibrations of the Heart", U.S. Appl. No. 10/900,570, Filed Jul. 28, 2004, 24 pgs.

Mower, Morton, U.S. Patent Office Patent Application Information Retrieval (PAIR) search results for U.S. Appl. No. 10/214,474, filed on Aug. 8, 2002, entitled *"Method and Apparatus for Treating Hemodynamic Disfunction"*, 3 Pages.

Ostadal, Petr, et al., " The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003),45-50.

Paolocci, Nazareno, et al., "Positive inotropic and lusitropic effects of HNO/NO- in failing hearts: Independence from β-adrenergic signaling", *PNAS*, vol. 100, No. 9, (Apr. 29, 2003),5537-5542.

Reiter, Michael J., et al., "Electrophysiological Effects of Acute Dilatation in the Isolated Rabbit Hear", *Circulation*, vol. 96, No. 11, (Dec. 2, 1997),4050-4056.

Ritter, P., et al., "New Method for Determining the Optimal Atrio-Ventricular Delay in Patients Place in DDD Mode for Complete Atrio-Ventricular Block", *NASPE* abstract #237, p. 885, (1995),3.

Salloum, Fadi, "Sildenafil Induces Delayed Preconditioning Through Inducible Nitric Oxide Synthase-Dependent Pathway in Mouse Heart", *Circulation Research*, 92, (Apr. 4, 2003),595-597.

Siejko, Krzysztof Z., "A Third Heart Sound Activity Index for Heart Failure Monitoring", U.S. Appl. No. 10/746,874, Filed Dec. 24, 2003, 41 pgs.

Siejko, Krzysztof Z., et al., "Method and Apparatus for Third Heart Sound Detection", U.S. Application No. 10/746,853, Filed Dec. 24, 2003, 40 pgs.

Smith, R.A., et al., "An intranet database for pacemaker patients", *International Journal of Medical Informatics*, 47, (1997), 79-82.

Suematsu, Yoshihiro, et al., "L-Arginine given after ischaemic preconditioning can enhance cardioprotection in isolated rat hearts", *European Journal of Cardio-thoracic Surgery*, 19, (2001),873-879.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003), 122-131.

Wofrum, Sebastian, et al., "Acute Reduction of Myocardial Infarct Size By a Hydroxymethyl Glutaryl Coenzyme A Reductase Inhbitor Is Mediated By Endothelial Nitric Oxide Synthase", *J. Cardiovas Pharmacol*, vol. 41, No. 3, (Mar. 2003),474-480.

Wunderlich, Carsten, "Acute Inhibition of Myoglobin Impairs Contractility and Energy State of iNOS-Overexpressing Hearts" *Circulation Research*, 2, (2003),1352-1358.

Hada, Yoshiyuki, et al., "Pulsus alternans determined by biventricular simultaneous systolic time intervals", *Circulation*, vol. 65, No. 3, (Mar. 1982),617-26.

Konta, Tsuyoshi, et al., "Significance of Discordant ST Alternans in Ventricular Fibrillation", *Circulation*, vol. 82, No. 6, Dec. 1990, American Heart Association,(1990),2185-2189.

Lee, Y. C., et al., "Pulsus alternans in patients with congestive cardiomyopathy", *Circulation*, vol. 65, No. 7, (Jun. 1982),1533-4.

Rubenstein, Donald S., et al., "Premature Beats Elicit a Phase Reversal of Mechanoelectrical Alternans in Cat Ventricular Myocytes", *Circulation*, vol. 91, No. 1, Jan. 1995, American Heart Association,(Jan. 1, 1995(,201-214.

Schaefer, S, et al., "Clinical and hemodynamic characteristics of patients with inducible pulsus alternans", *American Heart Journal*, vol. 115, No. 6, (Jun. 1988),1251-7.

Smith, Damon, et al., "Influence of the Aortic Component of the Second Heart Sound on Left Ventricular Maximal Negative dP/dt in the Dog", *Am. J. Cardiol.*, 55: 205, (1985),205-209.

Pastore, Joseph M., et al., "Method and Apparatus for Detecting Oscillations in Cardiac Rhythm with Electrogram Signals", U.S. Appl. No. 11/184,325, Filed Jul. 19, 2005, 22 Pages.

Bulgrin, J. R., et al., "Comparison of Short-Time Fourier, Wavelet and Time-Domain Analyses of Intracardiac Sounds", *Biomedical Sciences Instrumentation*, 29, (1993), 465-472.

Leatham, A, "Splitting of the First and Second Heart Sounds", *Lancet, 267 (6839)*, (Sep. 25, 1954), 607-614.

Obaidat, M.S., et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technological Challenges of the 1990s, (1992),856-862.

Wood, J. C., et al., "Time-Frequency Transforms: A New Approach to First Heart Sound Frequency Dynamics", *IEEE Transactions on Biomedical Engineering, 39 (7)*, IEEE Service Center, US,(Jul. 1, 1992),730-740.

METHOD AND APPARATUS FOR DETECTING ACOUSTIC OSCILLATIONS IN CARDIAC RHYTHM

FIELD OF THE INVENTION

This patent application pertains to methods and apparatus for cardiac rhythm management. In particular, it relates to the detections of oscillations in heart rhythm and its use by a cardiac rhythm management device.

BACKGROUND

Cardiac rhythm refers to the temporal pattern of electrical or mechanical activity in the heart. Cardiac rhythm management devices are implantable devices that provide electrical stimulation to selected chambers of the heart in order to treat disorders of cardiac rhythm. An implantable pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Cardiac rhythm management devices may also be used to treat tachyarrhythmias where the heart rhythm is too fast. In a type of pacing therapy called anti-tachycardia pacing, one or more pacing pulses are output during a cardiac cycle in an effort to interrupt the reentrant circuit causing a tachycardia. Other tachyarrhythmias, such as fibrillation, can be treated by devices that deliver a cardioversion/defibrillation shock when the tachyarrhythmia is detected.

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Heart failure refers to a clinical syndrome in which an abnormality of cardiac function causes a below normal cardiac output that can fall below a level adequate to meet the metabolic demand of peripheral tissues. It usually presents as congestive heart failure (CHF) due to the accompanying venous and pulmonary congestion. Heart failure can be due to a variety of etiologies with ischemic heart disease being the most common. Some heart failure patients suffer from some degree of AV block or are chronotropically deficient such that their cardiac output can be improved with conventional bradycardia pacing. Such pacing, however, may result in some degree of discoordination in atrial and/or ventricular contractions because pacing excitation from a single pacing site spreads throughout the myocardium via the conducting muscle fibers of either the atria or the ventricles, and not the faster specialized conduction pathways as in a physiological heart beat. Most pacemaker patients can still maintain more than adequate cardiac output with artificial pacing, but the diminishment in cardiac output may be significant in a heart failure patient whose cardiac output is already compromised. Intraventricular and/or interventricular conduction defects are also commonly found in heart failure patients and can contribute to cardiac dysfunction by causing unsynchronized contractions during intrinsic beats. In order to treat these problems, cardiac rhythm management devices have been developed that provide electrical pacing stimulation to one or more heart chambers in an attempt to improve the coordination of atrial and/or ventricular contractions, termed cardiac resynchronization therapy.

SUMMARY OF THE INVENTION

The present invention relates to an implantable cardiac rhythm management device that is configured to detect oscillatory behavior in the rhythm of the heart as reflected by alternations in the measured amplitudes of heart sounds, referred to herein as acoustic alternans. Acoustic alternans is indicative of alternations in the strength of systolic contractions and pulse pressure, a condition known as pulsus alternans. Pulsus altenans is generally taken by clinicians to indicate systolic dysfunction and possible heart failure. A cardiac rhythm management device may therefore also be configured to compensate for the decrease in cardiac output when acoustic altemans is detected by initiating or modifying the delivery of cardiac resynchronization therapy. Pulsus alternans is also highly correlated with oscillations in the electrical activity of the heart, called electrical alternans. Since electrical alternans is known to be potentially arrhythmogenic, the device may be further configured to adjust its operation when the condition is detected to deal with this situation. Such operational adjustments may relate to the manner in which either bradycardia pacing or anti-tachycardia pacing is delivered.

DETAILED DESCRIPTION

Figure 1:
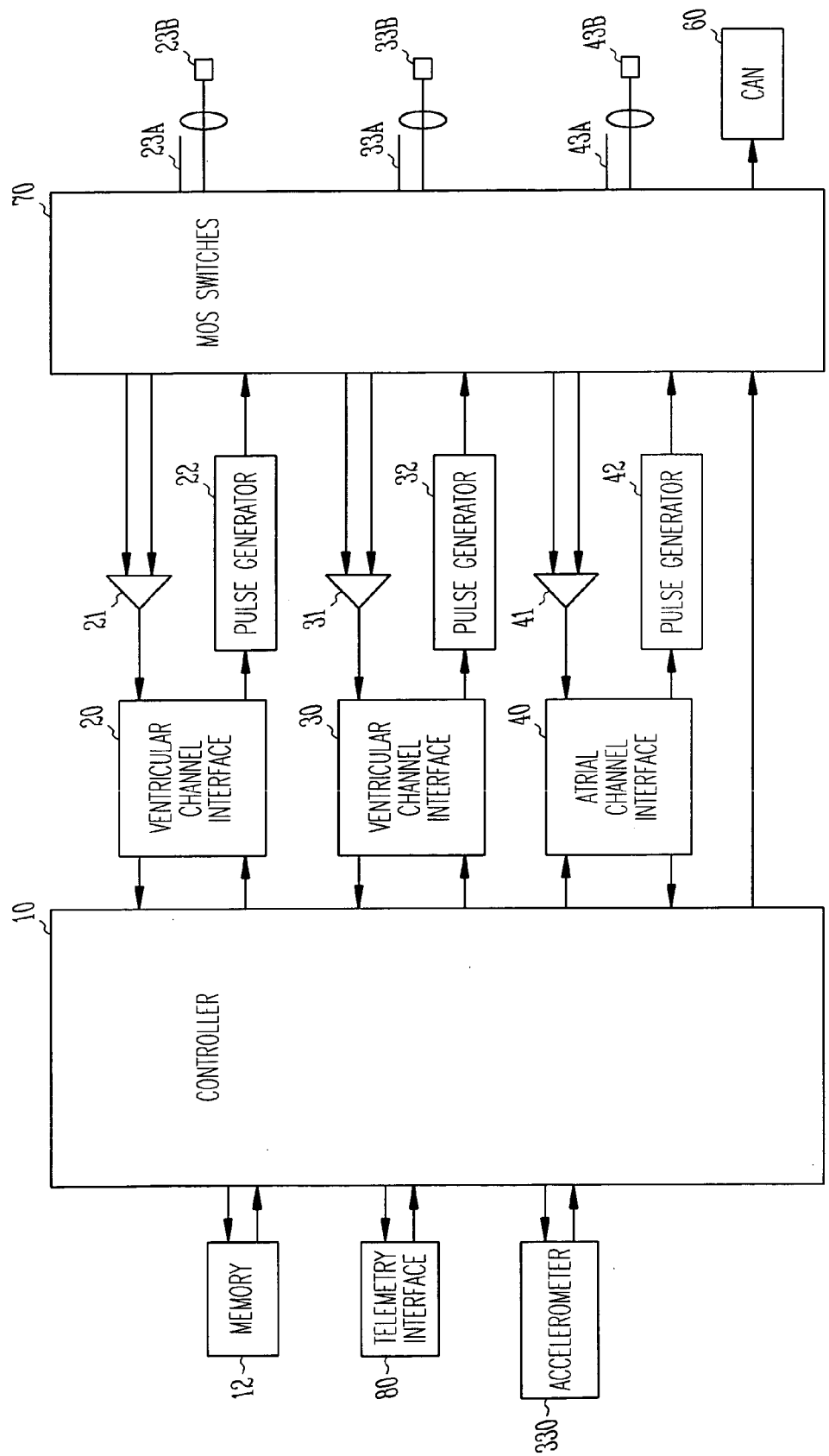
FIG. 1 is a system diagram of an exemplary cardiac rhythm management device.

Under certain conditions, some individuals exhibit oscillations in the mechanical function of the heart that result in alternations in pulse pressure, referred to as pulsus alternans. Pulsus alternans is generally taken by clinicians to indicate systolic dysfunction, particularly in the left ventricle. It would be useful for an implanted cardiac rhythm management device to be able to detect this condition when it arises so that the presence of the condition can be communicated to a clinician and, as explained below, so that the operating behavior of the device can be adjusted appropriately. Direct detection of blood pressure by an implantable device, however, is problematic. The present invention provides a method for detecting pulsus alternans by using alternations in the amplitudes of measured heart sounds, referred to herein as acoustic alternans, as a surrogate.

Pulsus alternans occurs due to a difference in the strength of systolic contractions during successive heart beats so that a strong beats alternate with weak beats. As explained below, the strength of a systolic contraction affects the velocity at which the AV and semilunar valves close, which closures are responsible for producing the first and second heart sounds, S1 and S2, heard during cardiac auscultation. Thus, alternating loud and soft heart sounds, or acoustic alternans, is directly reflective of pulsus alternans. Heart sounds may be detected and measured by an implantable device equipped with an accelerometer that responds to the acoustic vibrations transmitted through body fluids. Accelerometers are commonly used in pacemakers to measure the physical activity of the patient so that the pacing rate can be adjusted accordingly. By detecting and measuring the amplitudes of heart sounds during successive heart beats, acoustic alternans can be detected.

As noted above, certain cardiac rhythm management devices are designed to deliver pacing therapy in a manner that improves the coordination of both ventricles (or both atria) during systolic contractions, termed cardiac resynchronization therapy. The presence of pulsus alternans in such patients indicates that systolic function has been further impaired, and it may be beneficial for a device configurable for delivering resynchronization pacing to adjust its operating parameters to compensate for this when acoustic alternans, serving as a surrogate for pulsus alternans, is detected. For example, a device may be configured to deliver bradycardia pacing to one ventricle in a conventional manner or even no pacing under normal conditions. If acoustic alternans is detected, however, the device may be programmed to initiate resynchronization therapy by, for example, pacing both ventricles or one ventricle at multiple sites. In another embodiment, a device configured to deliver resynchronization pacing during normal conditions may adjust one or more operating parameters when acoustic alternans is detected so that the resynchronization pacing is modified. Examples of operating parameters that may be so adjusted are the biventricular delay interval between paces delivered to the right and left ventricles and the atrio-ventricular delay interval between an atrial pace or intrinsic sense and a subsequent ventricular pace.

The pattern of electrical excitation of the human heart may also exhibit oscillations during successive heart beats. This phenomena is referred to as electrical alternans and is usually indicative of a pathological state in which potentially dangerous cardiac arrhythmias are more likely to occur. Since the pumping action of the heart is due to the electromechanical coupling between electrical depolarization of myocardial cells and their mechanical contraction, electrical alternans and pulsus alternans may be different manifestations of the same underlying phenomena in certain cases. In any event, detection of acoustic alternans means that it is highly probable that electrical alternans is also present. Since the presence of electrical alternans in an individual may indicate that an arrhythmogenic condition exists, it may be deleterious for an implantable cardiac rhythm management device to deliver its therapy to the patient in a normal manner under such circumstances. In accordance with the invention, an implantable cardiac rhythm management device that detects acoustic alternans in the manner described above is also configured to adjust its operating behavior when alternans is detected. Such a device may deliver any kind of cardiac rhythm management therapy to the patient during normal conditions including bradycardia pacing, anti-tachycardia pacing, and/or cardioversion/defibrillation. Since it is known that electrical alternans occurs above a critical threshold heart rate, for example, bradycardia pacing at a rate above that critical threshold when electrical alternans is present may aggravate the situation. In one embodiment, a device configured to deliver bradycardia pacing adjusts its pacing rate to a lower value when acoustic alternans is detected. Rapid heart rates may also more readily trigger arrhythmias when an arrhythmogenic condition is present. In another embodiment, a device configured to deliver anti-tachycardia pacing lowers the threshold heart rate at which such therapy is initiated when acoustic alternans is detected in order to reduce the probability of an arrhythmia occurring.

1. Exemplary Hardware Platform

Cardiac rhythm management devices are usually implanted subcutaneously or submuscularly on a patient's chest and have leads threaded intravenously into the heart to connect the device to electrodes used for sensing and pacing. Leads may also be positioned on the epicardium by various means. A block diagram of a multi-site pacemaker having three sensing/pacing channels is shown in FIG. 1. (As the term is used herein, a "pacemaker" should be taken to mean any cardiac rhythm management device, such as an implantable cardioverter/defibrillator, with a pacing functionality.) Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber. The controller of the pacemaker is made up of a microprocessor 10 communicating with a memory 12 via a bidirectional data bus, where the memory 12 comprises a ROM (read-only memory) for program storage and a RAM (random-access memory) for data storage. The controller can be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. An accelerometer 330 enables the controller to adapt the pacing rate in accordance with detected changes in the patient's physical activity that indicate changes in exertion level and metabolic demand. A telemetry interface 80 is also provided for communicating with an external programmer.

The multiple sensing/pacing channels may be configured to deliver bradycardia pacing, cardiac resynchronization therapy, or anti-tachycardia pacing. Illustrated in FIG. 1 is a configuration with one atrial and two ventricular sensing/pacing channels for delivering biventricular pacing. Other embodiments may include additional sensing/pacing channels for multi-site pacing of an atrium and/or ventricle. The atrial sensing/pacing channel in FIG. 1 comprises ring electrode 43*a*, tip electrode 43*b*, sense amplifier 41, pulse generator 42, and an atrial channel interface 40 which communicates bidirectionally with the controller 10. The device also has two ventricular sensing/pacing channels that similarly include ring electrodes 23*a* and 33*b*, tip electrodes 23b and 33b, sense amplifiers 21 and 31, pulse generators 22 and 32, and ventricular channel interfaces 20 and 30. Each channel thus includes a pacing channel made up of the pulse generator connected to the electrode and a sensing channel made up of the sense amplifier connected to the electrode. The channel interfaces may include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude. For each channel, the same electrode pair is used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The time intervals between such senses can also be measured in order to detect tachyarrhythmias so that appropriate therapy can be delivered by the device. As described below, the controller may also be programmed to detect acoustic alternans and to adjust the manner in which pacing therapy is delivered by the device upon such detection. In one embodiment, the controller is programmed to detect acoustic alternans when the measured oscillations exceed a specified magnitude and to adjust the operating behavior of the device when acoustic alternans is detected.

2. Detection of Acoustic Alternans

When the heart beats, closure of valves brought about by pressure differentials in the heart are associated with audible heart sounds that can be heard by auscultation with a stethoscope. The first heart sound, designated S1, results when the AV valves (the mitral and tricuspid valves) close at the beginning of systole as the ventricular contraction causes a sudden backflow of blood toward the atria and against the valves. Due to the elastic nature of the valves, the movement of blood toward the atria causes the valves to bulge toward the atria and then recoil blood back toward the ventricle. This causes a period of reverberation that results in vibrations being transmitted through the blood and body tissues. The second heart sound, designated S2, similarly results when the semilunar valves (the aortic and pulmonary valves) close at the end of systole as the ventricular pressure drops. Because right-sided pressures are significantly lower than left-sided pressures, the amplitude of the heart sounds are primarily due to the closure of the mitral and aortic valves. During pulsus alternans, the strength of systolic contractions is alternately strong and weak. During a strong contraction, the mitral valve is stretched farther into the atria which then sets up a larger amplitude period of vibration. A stronger systolic contraction also causes an increased rate of pressure increase in the ventricle or dp/dt which may increase blood flow velocity. Thus the measured amplitude of both S1 and S2 would be expected to exhibit oscillatory behavior during pulsus alternans.

Figure 2:
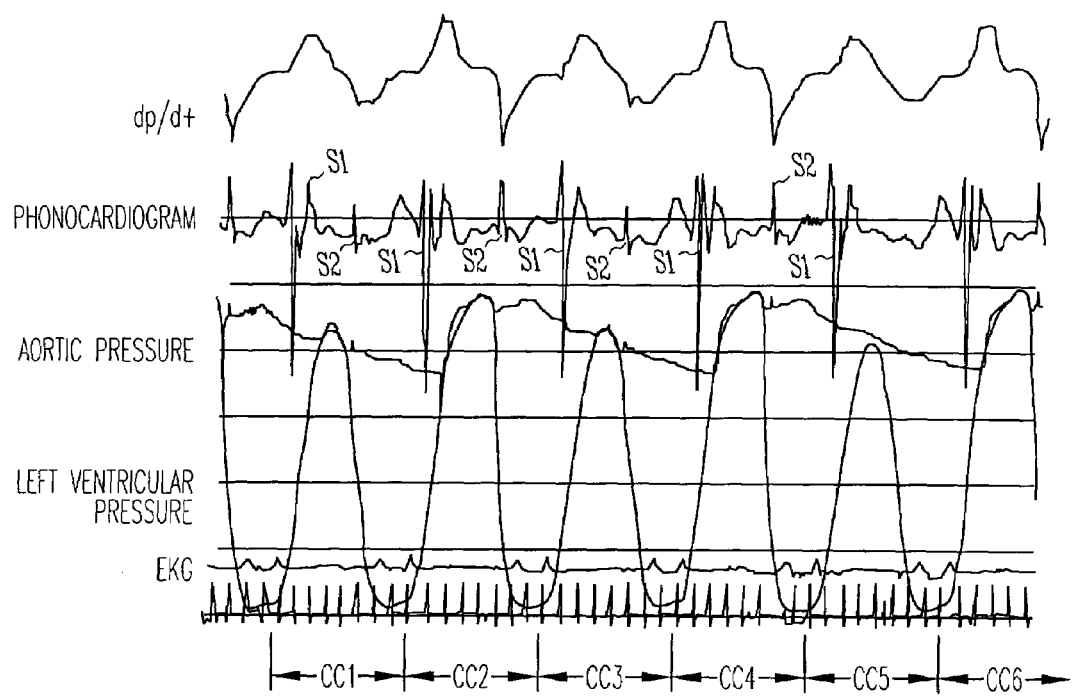
FIG. 2 illustrates pulsus alternans with accompanying acoustic alternans.

FIG. 2 shows an example of how pulsus alternans is reflected by acoustic alternans based upon data published in the literature (See Smith D., Craige E. *Am J Cardiol* 1985; 55:205). In the figure, five waveforms are shown with respect to a common time axis: a dp/dt waveform which is the time derivative of the left ventricular pressure and reflects the systolic force of contraction, a phonocardiogram which is the acceleration signal measured at the apex, the aortic pressure, the left ventricular pressure, and an electrocardiogram. Six cardiac cycles are shown, numbered CC1 through CC6. In each cardiac cycle, the beginning of ventricular systole is indicated by an R wave in the EKG. At about the same time as the R wave, there is a spike in the dp/dt waveform indicating ventricular contraction, and the left ventricular pressure begins to rise. When the left ventricular pressure exceeds the pressure in the left atrium, the mitral valve closes as indicated by the occurrence of an S1 heart sound in the phonocardiogram. Blood is ejected from the left ventricle into the aorta upon opening of the aortic valve as indicated by the simultaneous rise of both aortic and left ventricular pressure. As the ventricle relaxes, as marked by the T wave in the EKG indicating ventricular repolarization, the left ventricular pressure falls. When the left ventricular pressure falls below the aortic pressure, the aortic valve closes as indicated by the occurrence of an S2 heart sound in the phonocardiogram. Inspection of the left ventricular and aortic pressure waveforms reveals that the patient from whom this data was taken is exhibiting pulsus alternans, with cycles CC2, CC4, and CC6 being strong beats and cycles CC1, CC3, and CC5 being weak beats. It can also be seen that both S1 and S2 are of greater amplitude during the strong beats than during the weak beats. Although this amplitude difference could not be discerned by a clinician performing auscultation, an implantable device can measure the amplitudes with enough precision to allow the condition of acoustic alternans to be detected.

Figure 3:
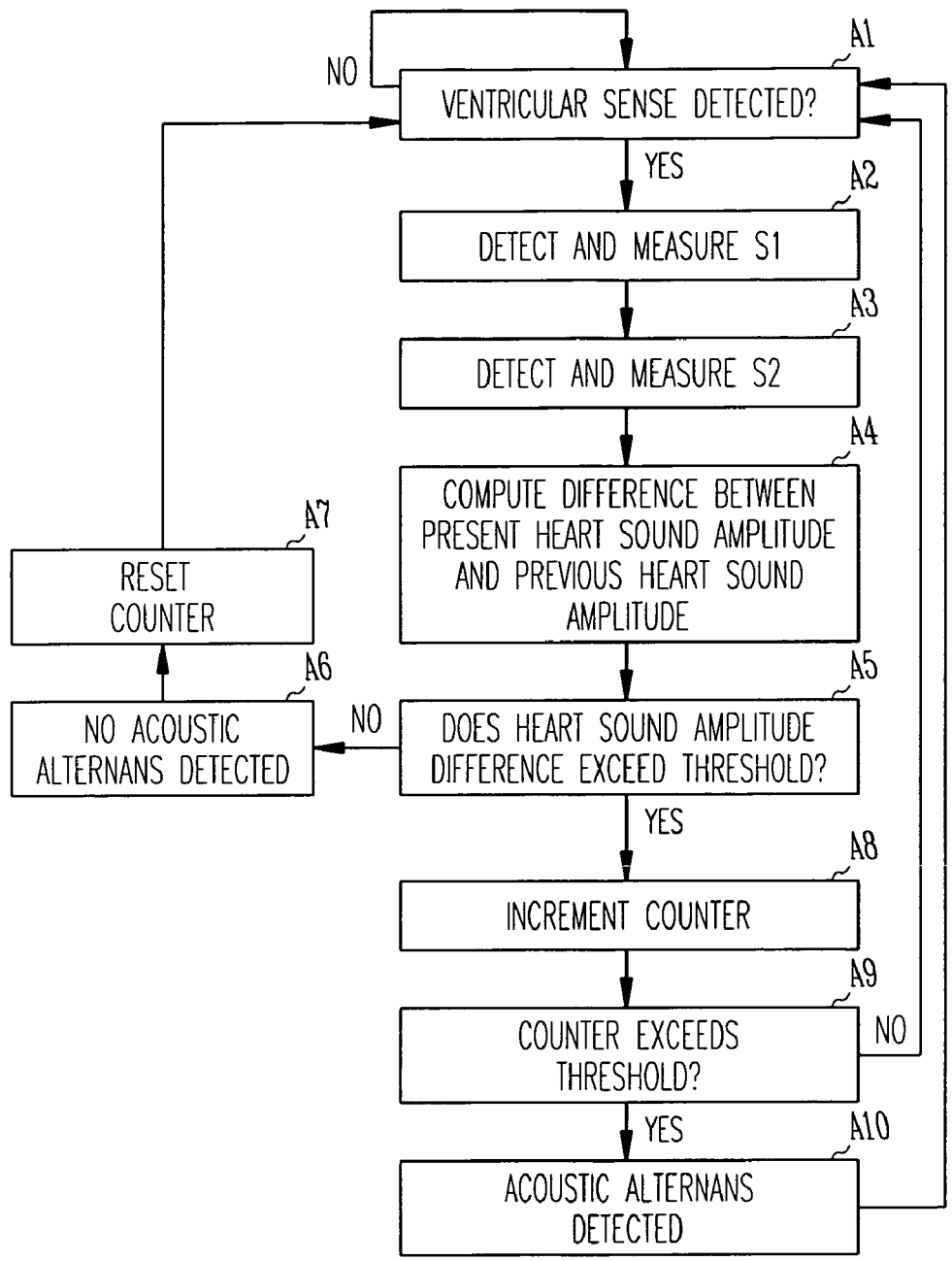
FIG. 3 illustrates an exemplary implementation of an algorithm for detecting acoustic alternans.

In order to detect acoustic alternans with specificity, specified threshold values may be employed so that the magnitude of the beat-to-beat oscillation must be above a certain value and must persist for a certain number of heart beats or period of time before acoustic alternans is detected. FIG. 3 shows an exemplary algorithm for detecting acoustic alternans based upon measurement of the amplitudes of the first and/or second heart sounds that can be implemented by the controller in conjunction with the phonocardiogram signal produced by an accelerometer or other microphonic device. In one embodiment of the invention, heart sounds may be detected without reference to any concomitant electrical activity in the heart, with the heart sounds themselves used to define cardiac cycles. In order to more reliably detect such heart sounds within each cardiac cycle, however, it may be advantageous to only look for them in a time window defined in relation to detected electrical cardiac activity. Accordingly, at step A1, the device waits for a ventricular sense (i.e., an R wave) indicating that a systolic contraction is beginning. After a ventricular sense and during a defined time window, the S1 sound is detected and its amplitude measured at step A2. During another subsequent defined time window, the S2 sound is detected and its amplitude measured at step A3. The time window defined for detection of S2 may optionally be defined with respect to the detection of ventricular repolarization (i.e., a T wave) indicating mechanical relaxation of the ventricles. A heart sound amplitude measurement is thus produced that can be compared with a heart sound amplitude measurement from the immediately preceding cardiac cycle. In various embodiments, the heart sound amplitude measurement may consist of the amplitude of S1, the amplitude of S2, or a value that is a function of the amplitudes of both S1 and S2. The difference between the heart sound amplitude of the present cardiac cycle and the heart sound amplitude of the previous cardiac cycle is then computed at step A4. If the heart sound amplitude difference exceeds a specified threshold, as determined at step A5, a counter that keeps track of the number of consecutive heart sound amplitude differences that exceed the threshold is incremented at step A8. Otherwise, a condition of no acoustic alternans is detected at step S6, the counter is reset at step A7, and the device waits for the next R wave at step A1. If the heart sound amplitude difference does exceed the threshold, after incrementing the counter at step A8, the counter's value is compared to a threshold count value at step A9. The threshold count value specifies the number of consecutive heart beats that the heart sound amplitude difference must be above threshold before acoustic alternans is detected. If the count exceeds the count threshold value, acoustic alternans is detected at step A10. The device then returns to step A1 and measures the heart sound amplitudes of the next heart beat.

3. Adjustment of Bradycardia Pacing Rate

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. Modern pacemakers are typically programmable so that they can operate in any mode which the physical configuration of the device will allow. Additional sensing of physiological data allows some pacemakers to change the rate at which they pace the heart in accordance with some parameter correlated to metabolic demand, called rate-adaptive pacing. Measurement of minute ventilation or body activity can be used to estimate metabolic demand for this purpose.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking and/or atrio-ventricular sequential pacing, another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing and atrio-ventricular sequential pacing attempt to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body. A pacemaker can also be configured to pace the atria on an inhibited demand basis, where an atrial escape interval is then defined as the maximum time interval in which an atrial sense must be detected after a ventricular sense or pace before an atrial pace will be delivered. The LRL in that case is the sum of the atrial escape interval and the AVI.

Rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which intrinsic atrial rates are unreliable or pathological. In a rate-adaptive pacemaker, for example, the LRL is adjusted in accordance with exertion level measurements such as from an accelerometer or minute ventilation sensor in order for the heart rate to more nearly match metabolic demand. The adjusted LRL is then termed the sensor-indicated rate.

Mechcanical alternans is indicative of electrical alternans which is known to occur only above a certain critical threshold heart rate that varies with the individual patient. A pacemaker operating in an inhibited demand mode, by enforcing a specified minimum heart rate, can be responsible in some cases for maintaining a heart rate that allows electrical alternans to occur. The controller may therefore be programmed to decrease the LRL by a specified amount upon detection of acoustic alternans. In the case of rate-adaptive pacing, the maximum sensor-indicated rate and/or the rate-response curve used to map an exertion level to a sensor-indicated rate may be adjusted to also result in a decreased LRL. Such a decrease in the LRL may be beneficial even if the alternans persists by making the triggering of an arrhythmia less likely.

4. Adjustment of Anti-tachycardia Pacing

The cardiac rhythm management device of FIG. 1 may be programmed with a plurality of selectable ATP pacing protocols that define the manner in which antitachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy can generally be divided into two classes: those that deliver one or more pulses in timed relation to detected depolarizations and those that deliver a continuous pulse train for a specified time beginning after a detected depolarization. Both types of ATP protocols attempt to block the reentrant depolarization wavefront causing the tachycardia with a second depolarizing wavefront produced by a pacing pulse. Protocols of the first group may vary according to parameters that define the number of pulses delivered and the particular timing employed. Protocols of the second group include so-called burst pacing in which a short train of pulses is delivered for a specified time and may vary according to parameters that define the duration, frequency, and timing of the pulses.

The device delivers ATP therapy or a defibrillation shock under programmed control of the microprocessor in response to sensed activity from the sensing channels. A sensing routine analyzes the electrical activity received from the sensing channels in order to detect a tachyarrhythmia, and the tachyarrhythmia is then classified as a tachycardia (i.e., a terminable tachyarrhythmia) or fibrillation based upon rate and/or other criteria. The device detects a ventricular tachyarrhythmia, for example, by counting ventricular senses received via the ventricular sensing channel in order to measure the heart rate and determine whether the rate exceeds a selected threshold value. Once a tachyarrhythmia is detected, the rhythm is classified into either a tachycardia or a fibrillation zone by comparing the heart rate to a fibrillation rate boundary or by other means such as assessing the stability of the rhythm. If the tachyarrhythmia is classified as terminable, a pacing routine executed by the microprocessor delivers ATP pulses in accordance with the parameters of a selected protocol.

As noted above, the object of anti-tachycardia pacing is to create a pace-induced wavefront that propagates into the re-entrant circuit of the tachycardia and extinguishes it. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy where pacing parameters affecting the magnitude and timing of the pulses can also be adjusted for each protocol. Ideally, a clinician would program the device to deliver pacing therapy using a protocol and parameters that will perform best for a particular patient's tachyarrhythmia.

Upon detection of acoustic alternans, the controller may be programmed to adjust the manner in which anti-tachycardia pacing is delivered that takes account of the greater potential for onset of an arrhythmic episode. In one example, the tachyarrhythmia rate threshold at which anti-tachycardia pacing is initiated is decreased so that the anti-tachycardia therapy is delivered sooner than in a normal mode of operation. Clinical testing of an individual patient may also reveal that certain anti-tachycardia pacing protocols are more successful than others in terminating a tachycardia preceded by acoustic alternans but less successful in terminating a tachyeardia not preceded by acoustic alternans. In those cases, the controller can be programmed to adjust the particular anti-tachycardia pacing protocol to be used for terminating a tachycardia and/or particular parameters defining that protocol when acoustic alternans is detected.

5. Adjustment of Cardiac Resynchronization Therapy

Cardiac resynchronization therapy is pacing stimulation applied to one or more heart chambers in a manner that restores or maintains synchronized contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. Resynchronization pacing, however, may also involve delivering paces to multiple sites of a heart chamber or pacing both ventricles and/or both atria in accordance with a resynchronization pacing mode as described below. Ventricular resynchronization pacing is useful in treating heart failure because, although not directly inotropic, resynchronization results in a more coordinated contraction of the ventricles with improved pumping efficiency and increased cardiac output. Resynchronization pacing of the atria may also be beneficial in certain heart failure patients, particularly for preventing the onset of atrial arrhythmias.

One way to deliver resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode. One such resynchronization pacing mode may be termed offset resynchronization pacing. In this mode, a first site is paced with a bradycardia mode, and a second site receives a resynchronization pace at an offset interval with respect to the pace delivered to the first site. The offset interval may be zero in order to pace both sites simultaneously, positive in order to pace the first site after the second, or negative to pace the first site before the second. For example, in biventricular resynchronization pacing, one ventricle is paced with a bradycardia mode while the contralateral ventricle receives resynchronization paces at the specified biventricular offset interval. The offset interval would normally be individually specified to optimize cardiac output in a particular patient. Ventricular resynchronization can also be achieved in certain patients by pacing at a single unconventional site, such as the left ventricle instead of the right ventricle. In such a mode, right ventricular senses may be used to trigger left ventricular paces or used to define an escape interval that upon expiration causes delivery of a left ventricular pace.

Cardiac rhythm management devices for delivering resynchronization therapy may be configured in a number of different ways and with a number of different parameter settings. These parameters can be initially programmed after implantation while a physician is monitoring the patient so that the resynchronization therapy is delivered optimally. When the pumping efficiency of the patient's heart deteriorates as may be indicated by detection of an oscillatory rhythm, however, modification of those parameters may be necessary for continued optimal treatment. Accordingly, the controller may be programmed to modify its resynchronization pacing parameters upon detection of acoustic alternans, with the exact manner in which such parameters are modified depending upon the individual patient's condition. Such parameter modifications may result in, for example, initiation of resynchronization pacing when such pacing is not normally delivered by the device, reconfiguration of pacing sites so that different cardiac sites are paced, adjustment of a biventricular offset interval for biventricular pacing modes, and adjustment of the atrio-ventricular interval for resynchronization pacing modes that employ atrial tracking or atrio-ventricular sequential pacing.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable cardiac rhythm management device, comprising:

an accelerometer for generating a phonocardiogram signal;

a controller for processing the phonocardiogram signal to detect heart sounds within the phonocardiogram signal and to measure oscillations in the amplitudes of the heart sounds during successive heart beats; and, wherein the controller is programmed to detect acoustic alternans when the measured oscillations exceed a specified magnitude and to adjust the operating behavior of the device when acoustic alternans is detected.

2. The device of claim 1 wherein the controller is programmed to detect oscillations in the amplitude of the first heart sound S1 in order to detect acoustic alternans.

3. The device of claim 1 wherein the controller is programmed to detect oscillations in the amplitude of the second heart sound S2 in order to detect acoustic alternans.

4. The device of claim 1 further comprising:
a sensing/pacing channel; and,
wherein the controller is programmed to deliver pacing therapy in accordance with a bradycardia mode, and further wherein the controller is programmed to decrease a programmed pacing rate when acoustic alternans is detected.

5. The device of claim 1 further comprising:
a sensing/pacing channel; and,
wherein the controller is programmed to deliver anti-tachycardia pacing therapy when a measured heart rate exceeds a specified tachycardia threshold rate, and further wherein the controller is programmed to decrease the tachycardia threshold rate when acoustic alternans is detected.

6. The device of claim 1 further comprising:
a first ventricular pacing channel;
a second ventricular pacing channel; and,
wherein the controller is programmed to deliver pacing therapy in accordance with a bradycardia mode, and further wherein the controller is programmed to initiate ventricular resynchronization pacing by delivering paces through both ventricular pacing channels when acoustic alternans is detected.

7. The device of claim 1 further comprising:
a first ventricular pacing channel;
a second ventricular pacing channel; and,
wherein the controller is programmed to deliver ventricular resynchronization pacing by delivering paces through both ventricular channels, and further programmed to adjust a resynchronization operating parameter when acoustic alternans is detected.

8. The device of claim 7 wherein the resynchronization operating parameter adjusted by the controller is an atrio-ventricular interval.

9. The device of claim 7 wherein the resynchronization operating parameter adjusted by the controller is a biventricular delay interval.

10. The device of claim 1 further comprising:
a first atrial pacing channel;
a second atrial pacing channel; and,
wherein the controller is programmed to deliver pacing therapy in accordance with a bradycardia mode, and further wherein the controller is programmed to initiate atrial resynchronization pacing by delivering paces through both atrial channels when acoustic alternans is detected.

11. A method for operating an implantable cardiac rhythm management device, comprising:
generating a phonocardiogram with an accelerometer;
processing the phonocardiogram signal to detect heart sounds within the phonocardiogram signal and to measure oscillations in the amplitudes of the heart sounds during successive heart beats; and,
detecting acoustic alternans when the measured oscillations exceed a specified magnitude and adjusting the operating behavior of the device when acoustic alternans is detected.

12. The method of claim 11 further comprising detecting oscillations in the amplitude of the first heart sound S1 in order to detect acoustic alternans.

13. The method of claim 11 further comprising detecting oscillations in the amplitude of the second heart sound S2 in order to detect acoustic alternans.

14. The method of claim 11 further comprising delivering pacing therapy in accordance with a bradycardia mode and decreasing a programmed pacing rate when acoustic alternans is detected.

15. The method of claim 11 further comprising delivering anti-tachycardia pacing therapy when a measured heart rate exceeds a specified tachycardia threshold rate and decreasing the tachycardia threshold rate when acoustic alternans is detected.

16. The method of claim 11 further comprising initiating ventricular resynchronization pacing by delivering paces to both ventricles when acoustic alternans is detected.

17. The method of claim 11 further comprising delivering ventricular resynchronization pacing by delivering paces through both ventricular channels and adjusting a resynchronization operating parameter when acoustic alternans is detected.

18. The method of claim 17 wherein the adjusted resynchronization operating parameter is an atrio-ventricular interval.

19. The method of claim 17 wherein the adjusted resynchronization operating parameter is a biventricular delay interval.

20. The method of claim 11 further comprising initiating atrial resynchronization pacing by delivering paces through both atrial channels when acoustic alternans is detected.

21. The method of claim 11 further comprising initiating ventricular resynchronization pacing by delivering left-ventricular only pacing when acoustic alternans is detected.

22. The method of claim 11 further comprising initiating ventricular resynchronization pacing by delivering multi-site pacing to the left ventricle when acoustic alternans is detected.

23. The device of claim 1 wherein the controller is programmed to detect acoustic alternans only when the measured oscillations exceeding a specified magnitude persists for a specified number of heartbeats or for a specified period of time.

24. The method of claim 11 further comprising detecting acoustic alternans only when the measured oscillations exceeding a specified magnitude persists for a specified number of heartbeats or for a specified period of time.

* * * * *